(12) United States Patent  (10) Patent No.: US 8,204,593 B2
Sheldon et al.  (45) Date of Patent: Jun. 19, 2012

(54) IDENTIFICATION AND TREATMENT OF JUNCTIONAL RHYTHMS

(75) Inventors: Todd J. Sheldon, North Oaks, MN (US); Harold Toby Markowitz, Roseville, MN (US)

(73) Assignee: Medtronic, Inc., Minneapolis, MN (US)

( * ) Notice: Subject to any disclaimer, the term of this patent is extended or adjusted under 35 U.S.C. 154(b) by 448 days.

(21) Appl. No.: 12/608,281

(22) Filed: Oct. 29, 2009

(65) Prior Publication Data

US 2011/0106196 A1 May 5, 2011

(51) Int. Cl.
*A61N 1/368* (2006.01)
(52) U.S. Cl. .................. 607/17; 607/9; 600/516
(58) Field of Classification Search .............. None
See application file for complete search history.

(56) References Cited

U.S. PATENT DOCUMENTS

| 4,284,082 A | 8/1981 | Funke |
| 5,417,714 A | 5/1995 | Levine |
| 5,534,016 A | 7/1996 | Boute |
| 5,741,308 A * | 4/1998 | Sholder ........................ 607/9 |
| 6,493,583 B1 | 12/2002 | Levine |
| 6,748,261 B1 * | 6/2004 | Kroll et al. .................. 600/510 |
| 7,174,209 B2 * | 2/2007 | Thompson et al. ............. 607/9 |
| 2001/0031994 A1 | 10/2001 | Mika |
| 2007/0255328 A1 | 11/2007 | Markowitz |

OTHER PUBLICATIONS (PCT/US2010/053184) PCT Notification of Transmittal of the International Search Report and the Written Opinion of the International Searching Authority, Mailed Mar. 2, 2011, 9 pages.

* cited by examiner

*Primary Examiner* — Kennedy Schaetzle
(74) *Attorney, Agent, or Firm* — Michael C. Soldner

(57) ABSTRACT

An implantable medical device and associated method provide atrial pacing and measure intervals between atrial pacing pulses and subsequently sensed ventricular events. A decreasing trend in the intervals indicative of a pre-junctional rhythm is detected. The atrial pacing pulse is delivered at a shortened atrial pacing pulse interval in response to detecting the decreasing trend to reduce the likelihood of a junctional rhythm.

23 Claims, 6 Drawing Sheets

IDENTIFICATION AND TREATMENT OF JUNCTIONAL RHYTHMS

TECHNICAL FIELD

The disclosure relates generally to implantable medical devices and, in particular, to an implantable medical device and associated method for identifying and treating a junctional rhythm.

BACKGROUND

A normal sinus cardiac rhythm arises from the sinoatrial (SA) node which acts as the heart's natural "pacemaker". Cardiac rhythms can arise from the atrioventricular (AV) node during periods of significant sinus bradycardia or complete AV block. The intrinsic rate originating from the AV node overtakes the intrinsic rate originating from the SA node. Rhythms originating from the AV node are commonly referred to as "junctional rhythms", "nodal rhythms" or "junctional ectopic tachycardia" (JET). Junctional rhythms can be highly symptomatic due to loss of AV synchrony. Symptoms may include shortness of breath, choking sensation, chest pain, fatigue, anxiety, dizziness, and confusion, all of which are generally considered to be signs of decreased cardiac output.

If junctional rhythms produce atrial beats closely followed by ventricular beats, dual chamber pacemakers may sense the atrial beat but the closely following sensed ventricular beat causes the pacemaker to presume the rhythm is normal sinus rhythm, and no pacing will occur. Similarly, junctional rhythms in which the ventricular beat is sensed before the atrial beat also result in no pacing as the pacemaker is inhibited by the series of ventricular sensed events. The junctional rhythm, which may be sporadic, remains undiagnosed with accompanying symptoms unexplained. Junctional rhythms remain challenging to manage using modern pacemakers. Ambulatory monitoring of patients using rhythm monitors designed to detect junctional rhythms has demonstrated that junction beats and junctional rhythms exist with a far higher frequency than previously understood in typical pacemaker or defibrillator (ICD) patient populations. A need remains, therefore, for an implantable cardiac pacing device and associated method for treating patients that experience junctional rhythms.

DETAILED DESCRIPTION

Figure 1:
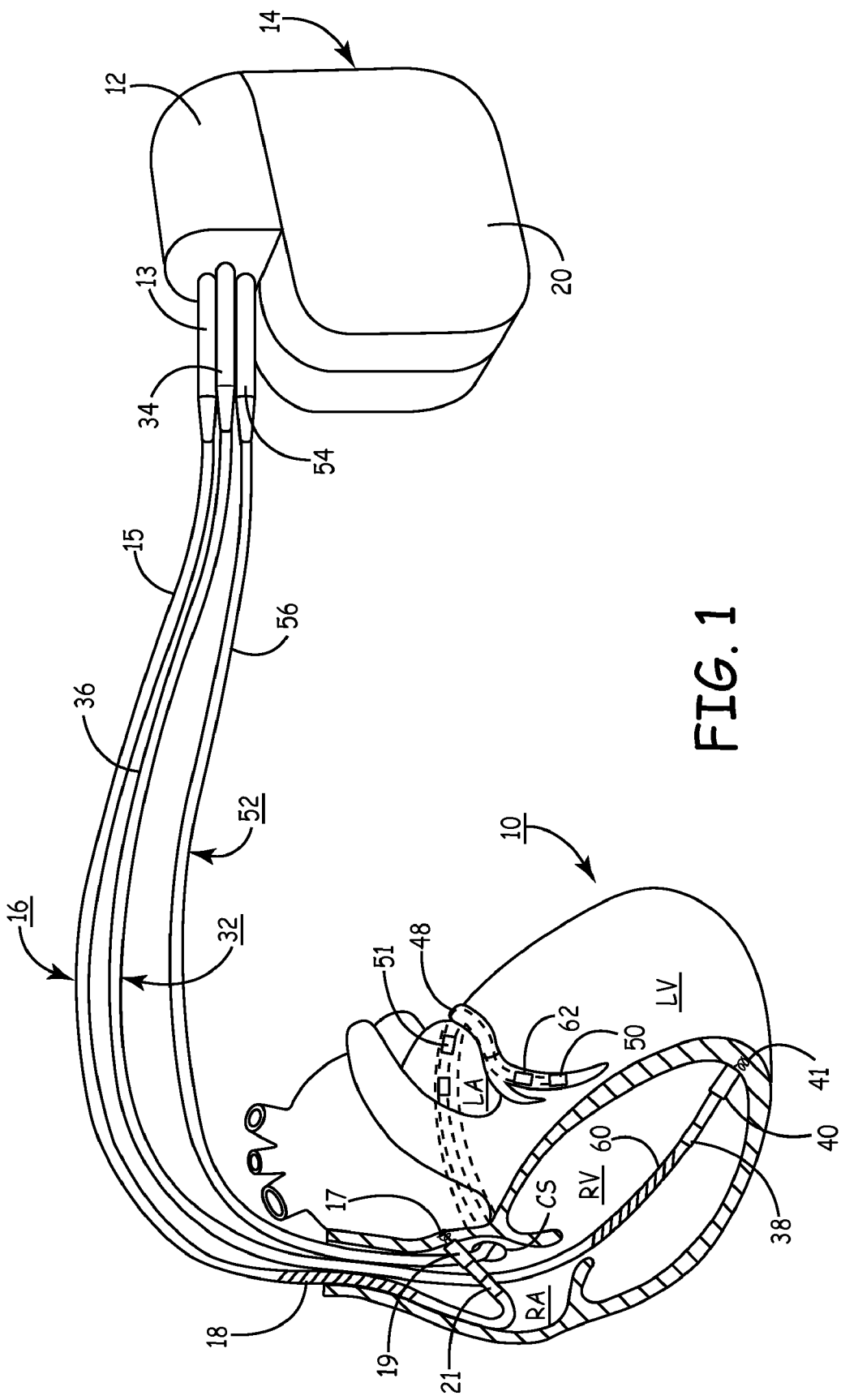
FIG. 1 depicts an implantable medical device (IMD) in which monitoring and pacing methods described herein may be implemented.

In the following description, references are made to illustrative embodiments. It is understood that other embodiments may be utilized without departing from the scope of the disclosure. For purposes of clarity, the same reference numbers are used in the drawings to identify similar elements. As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality.

FIG. 1 depicts an implantable medical device (IMD) 14 in which monitoring and pacing methods described herein may be implemented. Various embodiments of the disclosure may be implemented in numerous types of implantable medical devices capable of sensing cardiac signals, such as pacemakers, implantable cardioverter defibrillators (ICDs), ECG monitors, and hemodynamic monitors. IMD 14 is provided for sensing intrinsic heart activity and delivering cardiac stimulation pulses in the form of pacing, cardioversion or defibrillation therapy, as appropriate, to one or more heart chambers.

IMD 14 is shown in communication with a patient's heart 10 by way of three leads 16, 32 and 52. The heart 10 is shown in a partially cut-away view illustrating the upper heart chambers, the right atrium (RA) and left atrium (LA), and the lower heart chambers, the right ventricle (RV) and left ventricle (LV), and the coronary sinus (CS) in the right atrium leading into the great cardiac vein 48, which branches to form inferior cardiac veins. Leads 16, 32 and 52 connect IMD 14 with the RA, the RV and the LV, respectively. Each lead has at least one electrical conductor and pace/sense electrode. A remote indifferent can electrode is formed as part of the outer surface of the IMD housing 20. The pace/sense electrodes and the remote indifferent can electrode can be selectively employed to provide a number of unipolar and bipolar pace/sense electrode combinations for pacing and sensing functions.

RA lead 16 is passed through a vein into the RA chamber and may be attached at its distal end to the RA wall using an optional fixation member 17. RA lead 16 is formed with a connector 13 fitting into a connector bore of IMD connector block 12 for electrically coupling RA tip electrode 19 and RA ring electrode 21 to IMD circuitry housed within housing 20 via insulated conductors extending within lead body 15. RA tip electrode 19 and RA ring electrode 21 may be used in a bipolar fashion, or in a unipolar fashion with IMD housing 20, for achieving RA stimulation and sensing of RA EGM signals. RA lead 16 is optionally provided with a coil electrode 18 that may be used for delivering high voltage cardioversion/defibrillation pulses to heart 10 in response to the detection of tachycardia or fibrillation.

RV lead 32 is passed through the RA into the RV where its distal end, carrying RV tip electrode 40 and RV ring electrode 38 provided for stimulation in the RV and sensing of RV EGM signals, is fixed in place in the RV apex by a distal fixation member 41. RV lead 32 optionally carries a high-voltage coil electrode 60 for use in cardioverting and defibrillating heart 10. RV lead 32 is formed with a connector 34 fitting into a corresponding connector bore of IMD connector block 12. Connector 34 is coupled to electrically insulated conductors within lead body 36 and connected with distal tip electrode 40, ring electrode 38 and coil electrode 60.

Coronary sinus lead 52 is passed through the RA, into the CS and further into a cardiac vein 48 to extend the distal LV tip electrode 50 and ring electrode 62 alongside the LV chamber to achieve LV stimulation and sensing of LV EGM signals. The LV CS lead 52 is coupled at the proximal end connector 54 into a bore of IMD connector block 12 to provide electrical coupling of conductors extending from electrodes 50 and 62 within lead body 56 to IMD internal circuitry. In some embodiments, LV CS lead 52 could bear a proximal LA pace/sense electrode 51 positioned along CS lead body 56 such that it is disposed proximate the LA for use in stimulating the LA and/or sensing LA EGM signals.

In addition to the lead-mounted electrodes, IMD 14 may include one or more subcutaneous cardiac sensing electrodes (not shown) formed as uninsulated portions of the IMD housing 20 or included in the connector block 12. While a particular IMD system with associated leads and electrodes is illustrated in FIG. 1, numerous implantable cardiac monitoring, pacemaker or other IMD system configurations are possible, which may include one or more leads deployed in transvenous, subcutaneous, or epicardial locations. Methods described herein may also be implemented in a subcutaneous cardiac monitor, pacemaker or IMD system in which electrodes are formed as a part of the device housing and/or carried by subcutaneous leads. The lead and electrode arrangements will depend on the particular application.

IMD 14 is shown as a multi-chamber device capable of sensing and stimulation in three or all four heart chambers. It is understood that IMD 14 may be modified to operate as a dual chamber device or a single chamber (atrial pacing) device having dual chamber sensing capabilities. In the illustrative embodiments, described herein, methods for predicting, detecting and treating junctional rhythms generally relate to a pacemaker or ICD having at least dual chamber sensing and pacing. It is contemplated that the methods described, however, may be adapted for use in a single chamber device by using far-field sensing of ventricular events.

Figure 2:
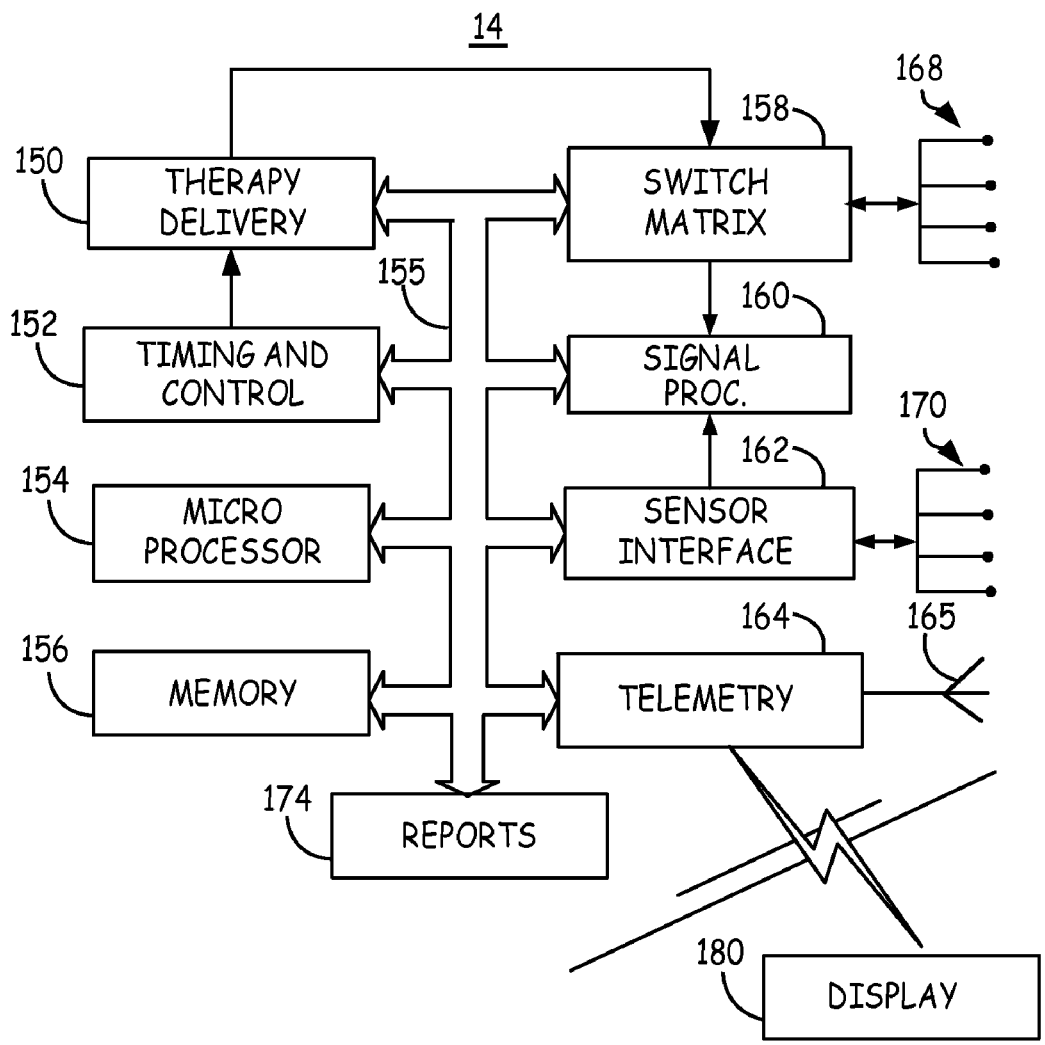
FIG. 2 is a functional block diagram of the IMD shown in FIG. 1 according to one embodiment.

FIG. 2 is a functional block diagram of the IMD 14 shown in FIG. 1 according to one embodiment. IMD 14 generally includes timing and control circuitry 152 and an operating system that may employ microprocessor 154 or a digital state machine for timing sensing and therapy delivery functions in accordance with a programmed operating mode. Microprocessor 154 and associated memory 156 are coupled to the various components of IMD 14 via a data/address bus 155. IMD 14 includes therapy delivery module 150 for delivering electrical stimulation therapies, such as cardiac pacing therapies and arrhythmia therapies including cardioversion/defibrillation shocks and anti-tachycardia pacing (ATP), under the control of timing and control 152.

As will be described herein, therapy delivery module 150 may be controlled by microprocessor 154 and timing and control 152 for delivering atrial pacing pulses in a manner that reduces the likelihood of junctional rhythms and for treating junctional rhythms when they are detected. In various embodiments, pre-junctional rhythms are detected and therapy delivery module 150 is controlled to deliver atrial pacing pulses at an increased rate to reduce the likelihood of the pre-junctional rhythm progressing to a junctional rhythm.

Therapy delivery module 150 is typically coupled to two or more electrodes 168 via an optional switch matrix 158. Electrodes 168 may correspond to any of the electrodes shown in FIG. 1. Switch matrix 158 may be used for selecting which electrodes and corresponding polarities are used for delivering electrical stimulation pulses.

Cardiac electrical signals are sensed for use in determining when an electrical stimulation therapy is needed and in controlling a stimulation mode and the timing of stimulation pulses. Electrodes 168 used for sensing are coupled to signal processing circuitry 160. Signal processor 160 includes sense amplifiers and may include other signal conditioning circuitry and an analog-to-digital converter. Electrical signals may then be used by microprocessor 154 or other control circuitry for sensing atrial events and ventricular events corresponding to intrinsic atrial and ventricular depolarizations, respectively, and for detecting physiological events, such as detecting and discriminating cardiac arrhythmias, detecting or predicting junctional rhythms, and detecting the need for pacing.

IMD 14 may optionally be coupled to one or more physiological sensors 170, which may include a motion sensor such as an accelerometer, a flow sensor, blood chemistry sensors such as an oxygen saturation sensor, activity sensors, an acoustical sensor, or other physiological sensors used for monitoring the patient. Physiological sensors may be carried by any lead extending from IMD 14, incorporated in or on the IMD housing or may be embodied as leadless sensors implanted in the body and in telemetric communication with the IMD or another device. Signals from sensors 170 are received by a sensor interface 162 which provides sensor signals to signal processing circuitry 160. Monitored signals may be used for sensing the need for delivering or adjusting a therapy under control of microprocessor 154. Monitored sensor signals may be analyzed to obtain diagnostic or prognostic data stored by IMD and made available to a clinician.

In various embodiments, IMD 14 includes rate responsive pacing in which an activity sensor, oxygen sensor, respiration sensor, or other sensor generating a signal correlated to metabolic demand, referred to herein generally as "demand sensor", or any combination of demand sensors, is used to compute a sensor-indicated rate (SIR). Timing and control module 152 responds to the SIR by adjusting an atrial pacing rate up or down between a programmed lower rate and a maximum upper rate.

As will be described in detail below, more aggressive rate responsive pacing can be achieved, for example, by increasing an upper rate limit, increasing an activities of daily living setting, and/or adjusting the slope of a transfer function applied to a demand sensor signal for setting the pacing rate. More aggressive rate responsive pacing may alternatively or additionally be achieved by altering the demand sensor(s) used for computing SIR or by altering the computations applied to the demand sensor signal(s) for computing the SIR.

The IMD operating system includes associated memory 156 for storing a variety of algorithms and parameter values that are used by microprocessor 154 to control IMD operation. Algorithms and control parameters used for determining a SIR and delivering rate responsive pacing, detecting arrhythmias, delivering arrhythmia therapy, monitoring AV delay, and detecting pre-junctional and junctional rhythms may be stored in memory 156. The memory 156 may also be used for storing data compiled from sensed EGM and physiological signals and/or relating to device operating history for telemetry out on receipt of a retrieval or interrogation instruction.

In one embodiment, memory 156 stores data relating to the detection of pre-junctional and junctional rhythms and the therapy delivery response to such detections. Stored data may be used to generate a junctional rhythm history report by reporting module 174. Trends in the frequency of pre-junctional and junctional rhythm detections may be useful to a clinician for patient diagnosis and in assessing the effectiveness of pacing therapies. Trends in the frequency of junctional rhythms may also be used by IMD 14 to automatically adjust pacing control parameters to reduce the frequency of junctional rhythm detections. Trends in pre-junctional and junctional rhythm detections may also be used by the IMD 14 for characterizing the changes in the heart rhythm that typically precede a junctional rhythm to enhance the sensitivity and specificity of pre-junctional rhythm detection criteria.

IMD 14 further includes telemetry circuitry 164 and antenna 165. Programming commands or data are transmitted during uplink or downlink telemetry between IMD telemetry circuitry 164 and external telemetry circuitry included in a programmer or monitoring unit. Report module 174 may compile data acquired by the IMD 14 for transmitting via telemetry circuitry 164 to an external display 180, which may be implemented in a programmer, personal computer, web-based or local network, or other communication device in communication with IMD 14. In one embodiment, data relating to pre-junctional and junctional rhythm detections and pacing therapy response is compiled in a medical report that is transmitted to display 180 to be presented in a text or graphical display to a clinician.

Figure 3:
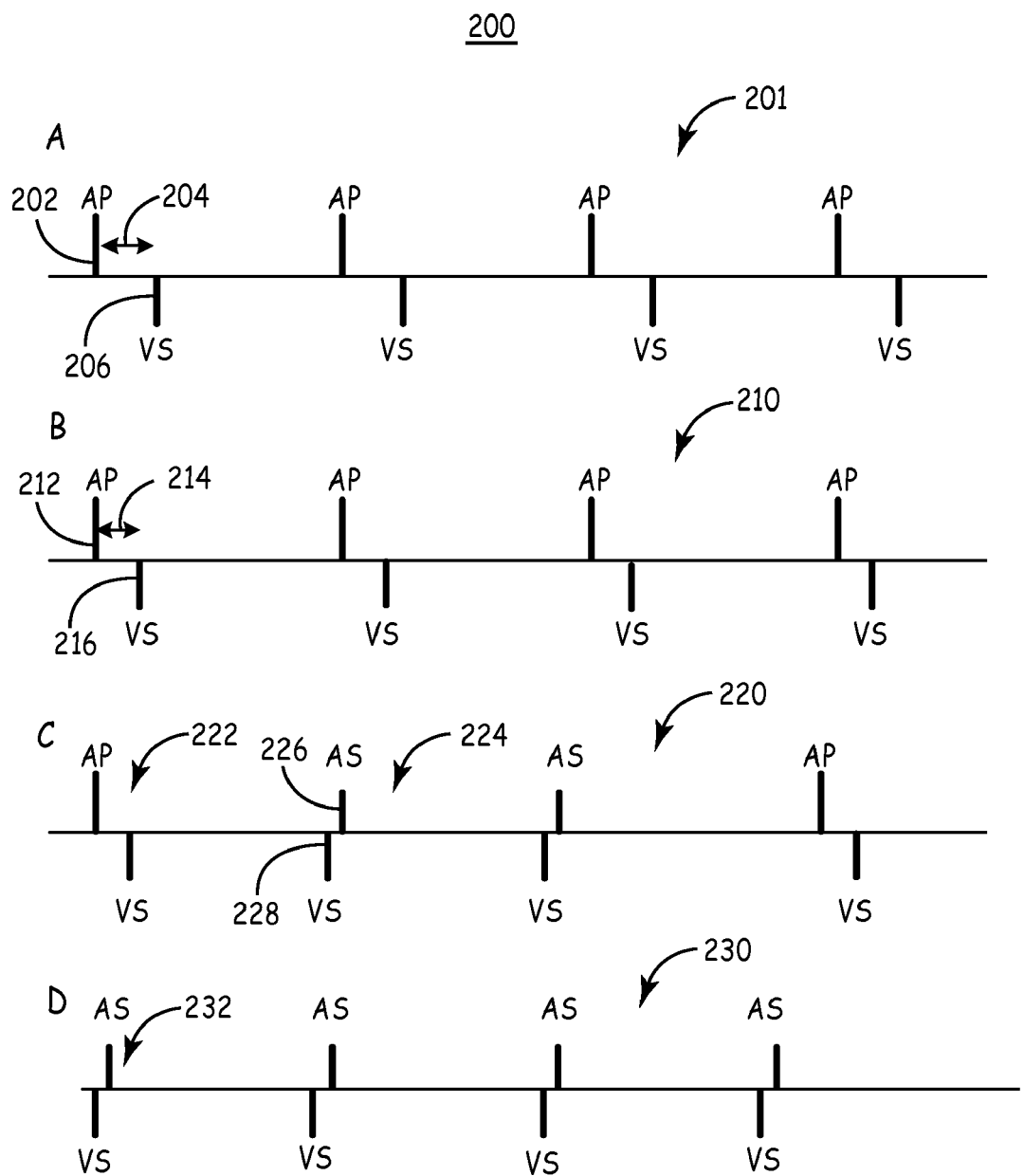
FIG. 3 is timeline illustrating the progression from an atrial paced rhythm to a pre-junctional rhythm, to a fused rhythm, finally evolving into a sustained junctional rhythm.

FIG. 3 is timeline 200 illustrating the progression from an atrial paced rhythm 201 to a pre-junctional rhythm 210, to a fused rhythm 220, finally evolving into a sustained junctional rhythm 230. Initially, during the atrial paced rhythm 201 as shown in Panel A, atrial pacing pulses (AP) 202 are followed by ventricular sense events (VS) 206 at a normal atrial-ventricular interval (AVI) 204. AVI 204 is referred to more specifically herein as an AP-VS interval in that it is an interval between an atrial pacing pulse 202 and subsequent ventricular sensed event 206. The atrial pacing pulses predominate in setting the cardiac rhythm 201.

A short time period later, e.g. twenty to thirty seconds later, the rhythm has become a pre-junctional rhythm 210, as shown in panel B. As used herein, a "pre-junctional rhythm" is a rhythm in which a decreasing trend in the AVI occurs, which, left untreated, would continue to decrease until the rhythm becomes a continuous junctional rhythm. The pre-junctional rhythm shown in panel B is characterized by an AP-VS interval 214 between atrial pacing pulses 212 and ventricular sense events 216 that is still considered within a normal AVI range but is demonstrating a decreasing trend. The decreasing trend is occurring within a relatively short period of time, e.g. in less than approximately one minute and typically less than approximately 30 seconds or even faster, within approximately 15 seconds.

The term "pre-junctional rhythm" as used herein also refers to a fused rhythm 220 as represented in Panel C. As the rhythm continues to progress toward a junctional rhythm, fusion of the atrial paced rhythm and an impending junctional rhythm may occur. A "fused rhythm" refers to a rhythm in which atrial paced beats 222 still occur with one or more intervening junctional beats 224, i.e. the atrial paced beats 222 and junctional beats 224 are mixed. The atrial paced beats 222 include an atrial pacing pulse followed by a ventricular sense event. These atrial paced beats 222 may in fact be fusion beats, in which the atria are and/or ventricles are partial activated by the pacing pulse and partially by the AV nodal activity. Junctional beats 224 occur when the heart beat originates from the AV node. An atrial sense event (AS) 226 occurs simultaneously or at a very short AV or VA interval with the ventricular sense event 228. As shown in this example, during junctional beats, the ventricular sense event 228 may sometimes be sensed earlier than the atrial event 226.

In Panel D, the junctional rhythm 230 has taken over and predominates. Over the course of approximately one to two minutes, the atrial paced rhythm 201 has progressed to a continuous junctional rhythm 230. Junctional beats 232 are sustained with no intervening atrial paced beats, and the junctional beats 232 can be seen to occur at a faster rate than the preceding atrial paced rhythm 201.

In the example of FIG. 3, the rhythm is originally a paced atrial rhythm 201 with no atrial sensed events shown. As will be described herein, an atrial preferred pacing mode of operation may be in effect such that atrial pacing is in effect the vast majority of the time. However it is recognized that aspects of the methods described herein may be implemented during atrial sensing such that a pre-junctional rhythm may include atrial sense beats with or without atrial paced beats.

Figure 4:
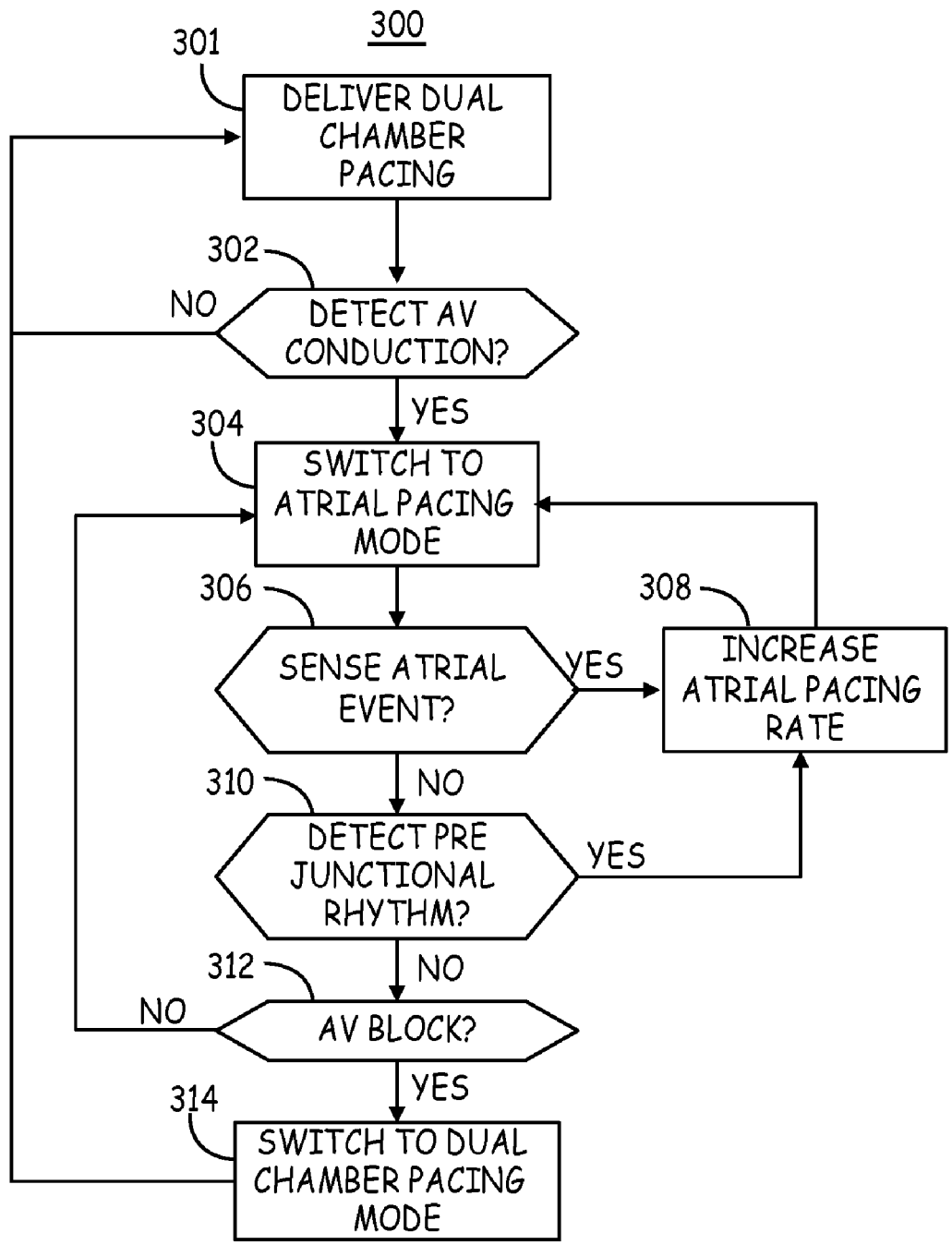
FIG. 4 is a flow chart of one method for controlling pacing therapy in a patient.

FIG. 4 is a flow chart 300 of one method for controlling pacing therapy in a patient. Flow chart 300 is intended to illustrate the functional operation of the device, and should not be construed as reflective of a specific form of software or hardware necessary to practice the methods described. It is believed that the particular form of software will be determined primarily by the particular system architecture employed in the device and by the particular detection and therapy delivery methodologies employed by the device. Providing software to accomplish the described functionality in the context of any modern medical device, given the disclosure herein, is within the abilities of one of skill in the art.

Methods described in conjunction with flow charts presented herein may be implemented in a computer-readable medium that includes instructions for causing a programmable processor to carry out the methods described. A "computer-readable medium" includes but is not limited to any volatile or non-volatile media, such as a RAM, ROM, CD-ROM, NVRAM, EEPROM, flash memory, and the like. The instructions may be implemented as one or more software modules, which may be executed by themselves or in combination with other software.

Methods described herein provide for the prediction, detection and treatment of junctional rhythms. In the illustrative embodiments, methods for predicting and detecting junctional rhythms and for controlling pacing therapy to prevent or treat a junctional rhythm are employed in an IMD programmed to operate in a minimum ventricular pacing (MVP) mode.

Naturally conducted or intrinsic ventricular depolarizations have been recognized as being preferable over ventricular pacing in general and pacing in the right ventricular apex in particular. In order to minimize or greatly reduce ventricular pacing, protocols have been developed that, in general, utilize an atrial based timing mode that promotes intrinsic conduction whenever possible. Illustrative protocols are described in U.S. Pat. No. 7,218,965 (Casavant), U.S. Pat. No. 6,772,005 (Casavant), and U.S. Pat. No. 7,248,924 (Casavant), all of which are incorporated herein by reference in their entireties. As used herein, an atrial based pacing mode is a mode that is programmed to pace in the atria, but only to sense in the ventricles. True single chamber atrial pacing would imply that only a single lead is present and ventricular activity may not be sensed in the ventricle nor would ventricular pacing be deliverable.

Atrial based pacing in general, as well as in the context of minimizing ventricular pacing as discussed above, may also include a rate response function. As a metabolic demand sensor indicates a need for increased cardiac output, the heart rate is elevated by increasing the atrial pacing rate.

In general, MVP operates by switching between an atrial pacing mode and a dual chamber pacing mode in response to changes in AV conduction. When intrinsic ventricular events are not sensed following an atrial pacing pulse due to AV block, the pacing mode switches to a dual chamber pacing mode. A periodic conduction check is performed during the dual chamber pacing mode to determine if AV conduction has returned. When AV conduction is detected, the pacing device switches the pacing mode back to the atrial pacing mode. Since MVP is generally a preferred operating mode in modern pacemakers, the methods relating to predicting, detecting and treating junctional rhythms will be described in the context of MVP. Because the atrial pacing pulse can sometimes cause a ventricular sense to occur during a blanking period, unnecessary ventricular back-up pacing pulses may be delivered. As the AV interval shortens, during a pre-junctional or junctional rhythm, ventricular pacing pulses may be delivered and the MVP protocol may cause a pacing mode switch from atrial to dual chamber pacing. As such, it is desirable to predict and preclude the progression of a junctional rhythm.

The process shown in flow chart 300 begins at block 301 in a dual chamber pacing mode. AV conduction checks are performed periodically at block 302, e.g. by delivering a single AAI pacing cycle or by extending the paced AV interval to a very long interval, to determine if AV conduction has returned. The return of AV conduction is evidenced by an intrinsically-conducted, sensed ventricular event following an atrial pacing pulse. If AV conduction is not detected, the dual chamber pacing mode continues at block 301. If AV conduction is detected, the pacing device switches to an atrial pacing mode at block 304.

In addition to operating in the context of MVP, methods described herein operate in the context of atrial preferred pacing (APP). In an APP mode of operation, if an atrial sense event occurs at block 306, the atrial pacing rate is increased by a small increment at block 308 to maintain overdrive pacing of the atria, thereby reducing the likelihood of intrinsic atrial activity. An APP mode of atrial pacing is generally used to reduce the likelihood of atrial tachycardia.

In addition to sensing an intrinsic atrial event, detection of a pre-junctional rhythm at block 310 causes the atrial pacing rate to be increased at block 308. Detection of pre-junctional rhythms will be described in greater detail below. Atrial pacing continues until AV block is detected at block 312. An AV block detection triggers a pacing mode switch back to dual chamber pacing at block 314. AV block detection at block 312 may be defined according to various criteria. In one embodiment, a mode switch back to dual chamber pacing occurs if AV conduction is absent (i.e. no ventricular sense event) in at least two out of four consecutive cycles during atrial pacing.

Figure 5:
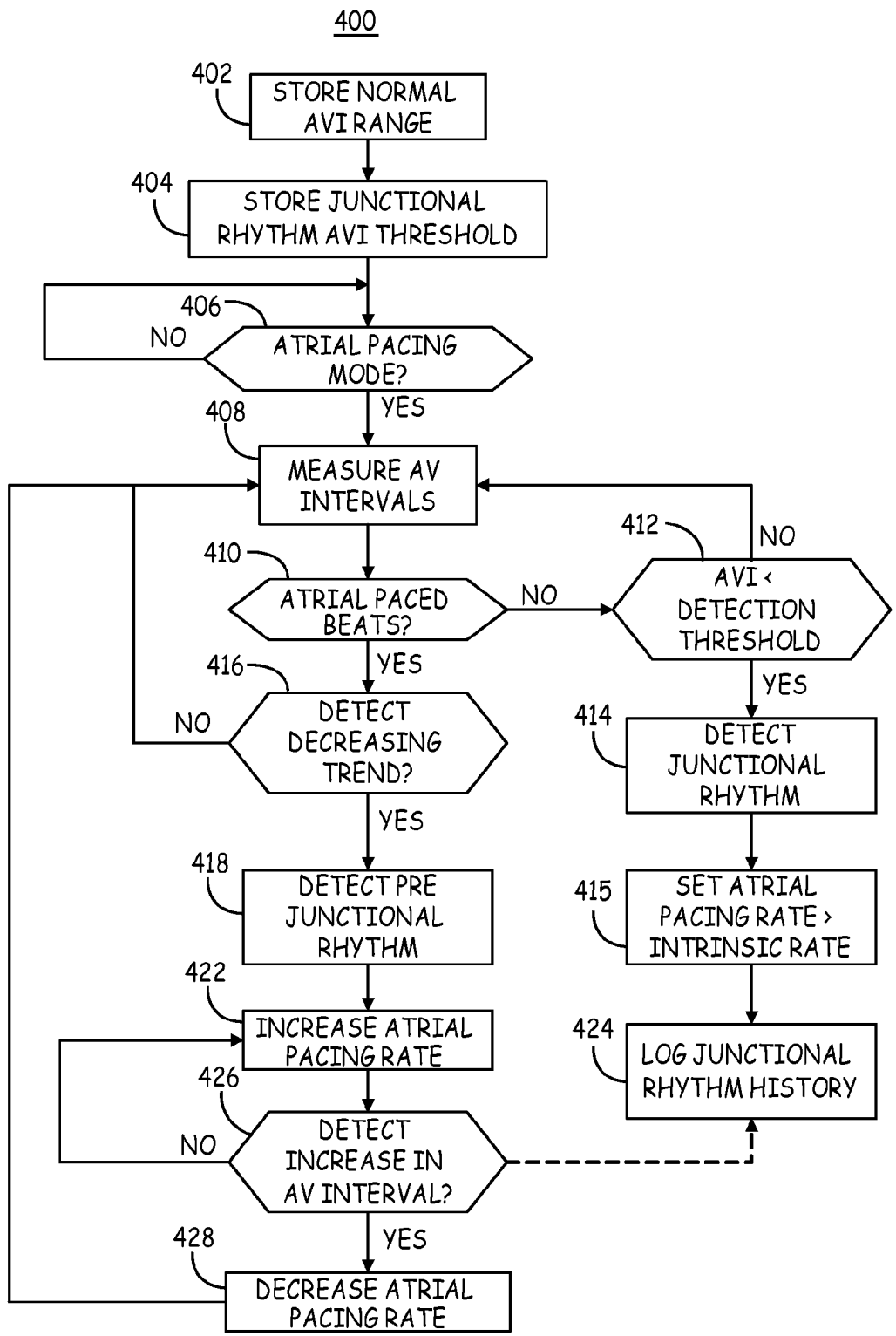
FIG. 5 is a flow chart of a method for controlling atrial pacing which includes detecting a pre-junctional rhythm.

FIG. 5 is a flow chart 400 of a method for controlling atrial pacing which includes detecting a pre-junctional rhythm. At block 402, a normal AVI range is stored. A normal AVI range is the range of AV intervals expected to occur between atrial paced and normally conducted ventricular sense events and may include AV intervals expected between atrial sensed events and ventricular sensed events during sinus rhythm. A stored normal AVI range may be programmed by a clinician based on clinical or individual patient data.

Alternatively, a learning process may be performed automatically by the IMD to determine a normal range of AV intervals during sustained atrial paced rhythms. The learning process may involve determining a minimum and a maximum AVI during a sustained atrial paced rhythm or determining average minimum and maximum AV intervals during multiple sustained atrial paced rhythms. The learning process may alternatively include determining an average AVI, maximum and/or minimum AVI and storing an AVI range based on percentiles of the average, maximum or minimum AVIs.

A sustained atrial paced rhythm may be defined according to varying criteria but is generally an atrial paced rhythm that includes a specified number of uninterrupted atrial paced beats and is not followed by a different rhythm for at least a specified time interval, e.g. at least one minute. For example, if the patient experiences a sustained atrial paced rhythm that progresses to a junctional rhythm or back to a dual chamber paced rhythm, the last one minute of the sustained atrial paced rhythm is not used for computing a normal AVI range since changes in the AVI may occur as the heart rhythm is transitioning into a different rhythm.

At block 404, a sensed AVI threshold for detecting a junctional rhythm is stored. The detection threshold will typically be an AVI less than the normal AVI range during an atrial paced rhythm. The detection threshold may correspond to a lower boundary of the normal AVI range. The detection AVI threshold will be applied to atrial sensed beats, not atrial paced beats, and would include intervals in which the ventricular sensed event occurs earlier than the atrial sensed event. The detection AVI may be more specifically referred to as an AS-VS interval threshold in that the threshold will be applied only to non-atrial paced beats. Atrial paced beats are not used to detect a junctional rhythm or beat because when the junctional rhythm takes over and becomes sustained, atrial pacing will be inhibited by the atrial depolarizations arising from the junctional rhythm.

In summary, the AVI threshold stored at block 404 is a detection threshold that is applied to atrial sensed events. The normal AVI range stored at block 402 used for detecting a pre-junctional rhythm is applied to atrial paced beats. In some embodiments, the AVI normal range criteria may be applied to both atrial paced and atrial sensed events for detecting pre-junctional rhythms whereas the detection AVI threshold is only applied to atrial sensed events.

While unlikely, it is possible that, in some embodiments, the detection AVI threshold falls within the stored normal AVI range since the detection threshold is applied only to atrial sensed beats and the normal AVI range will be applied to atrial paced beats. A normal atrial-paced AVI can have a different expected range than a normal sensed AVI.

At block 406, the process continues to block 408 if the pacing device is operating in an atrial pacing mode. If operating in a dual chamber pacing mode, the process waits until a pacing mode switch occurs to an atrial pacing mode. If a dual chamber pacing mode is in effect, the assumption is that the ventricular pacing pulses are capturing the ventricles and regulating the ventricular rhythm, thereby precluding the possibility of a junctional rhythm.

During atrial-only pacing, however, a junctional rhythm could take over the atrial paced rhythm if the AV nodal activity is generating an intrinsic rate faster than the presiding atrial pacing rate. During the atrial pacing mode, AV intervals are measured at block 408. AV interval measurements may include both AS-VS intervals and AP-VS intervals. If there are any atrial paced beats, as determined at block 410, the measured AV intervals are analyzed at block 416 to determine if a decreasing trend in AV intervals is occurring. When APP is operating, atrial pacing should predominate and most if not all beats will be atrial paced beats. In this case, the AV intervals will be AP-VS intervals. However, if a junctional rhythm is present, there may be no atrial paced beats in which case the AV intervals (AS-VS intervals) are compared to the detection threshold at block 412.

If no atrial paced beats are present (block 410) and the AS-VS intervals meet junctional rhythm detection criteria at block 412, a junctional rhythm is detected at block 414. The junctional rhythm detection criteria are based on the detection threshold stored at block 404. The detection criteria may require one or more beats each having, or averaging, an AVI less than the AVI threshold stored at block 404.

The detected junctional rhythm is treated by increasing the atrial pacing rate at block 422 above the sensed, intrinsic atrial rate. The detected junctional rhythm and related data is logged in memory at block 424 for tracking the patient's junctional rhythm history. By tracking the patient's frequency of junctional rhythm detections, a determination can be made if early detection and treatment of pre-junctional rhythms is effective in reducing the frequency of junctional rhythms.

If atrial paced beats are detected at block 410, the measured AV intervals are analyzed at block 416. The intervals that are analyzed may be intervals measured only during paced atrial beats, i.e. AP-VS intervals. Alternatively, AV intervals analyzed at block 416 may include both AP-VS intervals and AS-VS intervals measured using atrial sensed events.

Numerous methods may be conceived for detecting a decreasing trend in AVI. A decreasing trend may be detected based on a change from a previously measured baseline AVI to a decreased AVI within the stored normal AVI range. In some embodiments, a decreasing trend may be detected based on a cumulative sum of differences between consecutively measured AV intervals. If the cumulative sum reaches a negative threshold, indicating progressively decreasing AV intervals, a pre-junctional rhythm is detected. In other embodiments, a comparison of a running average to a previously determined running average may be used to detect a decreasing trend.

Criteria for detecting a decreasing trend may include both a magnitude of the decrease and a time interval within which the decrease must occur. A gradual decrease in AVI that occurs over hours or days is not evidence of a pre-junctional rhythm. A decrease in AVI that occurs in less than approximately one minute, for example within approximately 20 or 30 seconds, may signify progression toward a junctional rhythm.

In the absence of a decreasing trend, the process returns to block 408 to continue measuring AV intervals to monitor for junctional and pre-junctional rhythms. A pre-junctional rhythm is detected at block 418 in response to detecting a decreasing trend at block 416. The atrial pacing rate is increased at block 422.

The atrial pacing rate may be increased directly, in a gradual or step-wise manner to a higher rate, which may be a predefined increment above the current pacing rate. In alternative embodiments, the atrial pacing rate is effectively increased by adjusting other pacing control parameters. For example, adjustments may be made to rate response parameters used to compute a SIR using a demand sensor signal or control parameters used in adjusting the current pacing rate to a computed SIR. Junctional rhythms typically occur during periods of patient inactivity and tend to be less common during rest or at night. As such, providing a more aggressive rate response to a demand sensor signal may decrease the likelihood of a detected pre-junctional rhythm progressing to a junctional rhythm.

To increase the effective atrial pacing rate at block 422 in response to a pre-junctional rhythm detection, a maximum sensor-indicated upper rate may be increased. Additionally or alternatively, a transfer function or look-up table stored in pacing device memory that relates demand sensor output to a SIR may be adjusted to produce a higher SIR for a given demand. The greater the slope of a transfer function defining the relationship between the demand sensor output and the SIR, the more aggressive the rate response will be. In some embodiments, the implantable device stores a family of transfer functions or look-up tables which can be selected to provide more or less aggressive rate response. The transfer function or look-up table may be adjusted in response to detecting a pre-junctional rhythm to provide more aggressive rate responsive pacing.

In some embodiments, dual slope rate response pacing may be provided. Dual slope rate response pacing is controlled in part by programming an activities of daily living (ADL) rate intermediate a programmed lower rate and upper pacing rate. A range of pacing rates occurring between the lower rate and the ADL rate provides a desired rate response during normal daily activities of the patient, such as getting out of bed, moving about the house, etc. If a pre-junctional rhythm is detected, one or both of the ADL rate and the upper pacing rate may be increased at block 422 to effectively increase the current atrial pacing rate.

The range of pacing rates occurring between the ADL rate and the upper pacing rate defines an exertion range corresponding to more strenuous patient activity. Two different transfer functions or look-up tables may be selected for converting a demand sensor output to a SIR for the two different ADL rate range and exertion rate range. One or both of these transfer functions may be adjusted in response to detecting a pre-junctional rhythm. Moreover, if a pre-junctional rhythm is detected and the heart rate is within the exertion rate range, parameters affecting computation of the SIR in the exertion rate range may be adjusted for a more aggressive rate response in this range while leaving the rate response in the ADL range unchanged.

Other parameters that may be implemented for controlling rate response pacing include an attack constant which controls how quickly a sensor indicated rate may increase in response to increased demand sensor output. In other words, the attack constant controls how quickly the pacing rate is increased in response to increased demand sensor output. A decay constant may control how quickly the sensor indicated rate may decrease in response to decreased demand sensor output. One or both of the constants may be adjusted in response to detecting a pre-junctional rhythm to control how quickly the pacing rate changes in response to demand sensor output.

The pacing device may be provided with more than one demand sensor. Each demand sensor may be used individually or in different combinations for computing a SIR. If a pre-junctional rhythm is detected, the pacing device may determine which demand sensor or combination of sensors provides a more aggressive rate response than the demand sensor(s) currently being used to compute SIR. For example, a respiration sensor may provide a lower SIR than an activity sensor or vice versa. In another example, a combination of respiration sensor output and activity sensor output may provide a lower SIR than one or both of the sensors alone. A different demand sensor or combination of demand sensors may be selected at block 422 to effectively increase the atrial pacing rate in response to detecting a pre-junctional rhythm by using a demand sensor or combination of sensors resulting in more aggressive rate responsive pacing.

After increasing the atrial rate, directly or indirectly by adjusting rate response control parameters, the AV intervals continue to be measured at block 426 to determine if an increase in AV intervals is detected indicating successful avoidance of a junctional rhythm. An increase in AV intervals may be detected at decision block 426 by determining that the decreasing trend or the pre-junctional rhythm detection criteria applied at block 416 and 418 are no longer being met. Alternatively, a different set of criteria may be applied at block 426 for detecting an increasing trend in AV intervals. If the decreasing trend in AV intervals has not been disrupted or a pre-junctional rhythm is still being detected at block 428, the atrial pacing rate is again increased at block 422.

Once a pre-junctional rhythm has been initially detected at block 418, and the atrial pacing rate has been increased for the first time, criteria applied at block 422 may include determining if the pre-junctional rhythm is still being detected at the higher pacing rate using more aggressive detection criteria than used for the initial detection. A more aggressive detection, e.g. using fewer heart beats, allows quicker redetection of the pre-junctional rhythm than criteria applied upon initial detection of the pre-junctional rhythm. Quicker redetection of the pre-junctional rhythm after an initial atrial rate increase would allow the atrial pacing rate to continue to be increased in a step-wise or gradual manner after relatively short periods of time required for redetection. By increasing the atrial rate to a rate that is higher than a potential junctional rhythm, the junctional rhythm may be avoided.

Rate increases applied at block 422 in response to an initial detection and upon repeated detection of a pre-junctional rhythm may include any combination of a direct increase applied to the current atrial pacing rate and/or adjustments to parameters used to compute the SIR. For example, upon initial detection, adjustment to SIR control parameters may be made initially at block 422. If the pre-junctional rhythm is still detected after adjusting an SIR control parameter, the atrial rate may be increased directly, e.g. by a predetermined increment, at block 422.

When the atrial pacing rate is increased in response to detecting a pre-junctional rhythm, the atrial pacing rate adjustments and associated rhythm data may be logged in the junctional rhythm history at block 424. A clinician using the logged data may then evaluate how often a pre-junctional rhythm is being detected and treated and based on that data extrapolate the frequency that a predicted junctional rhythm is successfully avoided.

If an increase in AV interval is detected at block 426, signifying successful reversal of the pre-junctional rhythm, the atrial pacing rate may be decreased again at block 428. An interval of time or number of cardiac cycles over which increased or increasing trend in AV intervals is maintained may be required before beginning to decrease the atrial pacing rate at block 428. The atrial pacing rate may be decreased directly or indirectly by adjusting rate response control parameters. The atrial pacing rate may be reduced in a gradual or step-wise manner. After decreasing the atrial pacing rate, AV intervals continue to be monitored by returning to block 408 to detect any evidence of a return to a pre-junctional rhythm so that the atrial rate can be increased again as needed. Criteria applied at block 418 for re-detecting a pre-junctional rhythm during the process of backing down the increased atrial pacing rate may be more aggressive than the detection criteria used for initial detection of the pre-junctional rhythm.

The method shown in FIG. 4 can be implemented in a pacing device operating in a MVP mode with APP in effect. Thus, the absence of atrial paced beats during an atrial pacing mode is evidence that a junctional rhythm has taken over. In some embodiments, APP may not be in effect. If APP is not in effect, atrial sensing may be occurring during a normal sinus rhythm during an atrial pacing mode such that atrial pacing pulses are inhibited. In this case, both of the junctional rhythm detection criteria (block 412) and the pre-junctional rhythm detection criteria (block 416) may be applied simultaneously to measured AS-VS intervals to determine if a pre-junctional or junctional rhythm is detected.

In the illustrative embodiments described herein, the response to a detected pre-junctional rhythm includes adjusting the pacing therapy. In other embodiments, methods described for detecting pre-junctional rhythms may be implemented in an implantable medical device for monitoring and diagnostic purposes without providing a therapeutic response. The frequency of junctional rhythms and pre-junctional rhythms detected using the methods described herein, and characteristic features of the pre-junctional rhythms such as the heart rate and rate of AVI decrease, may be characterized by detecting these events and storing related data. Such data made available to a clinician allows the clinician to diagnose a patient having junctional rhythms and make appropriate treatment decisions.

Figure 6:
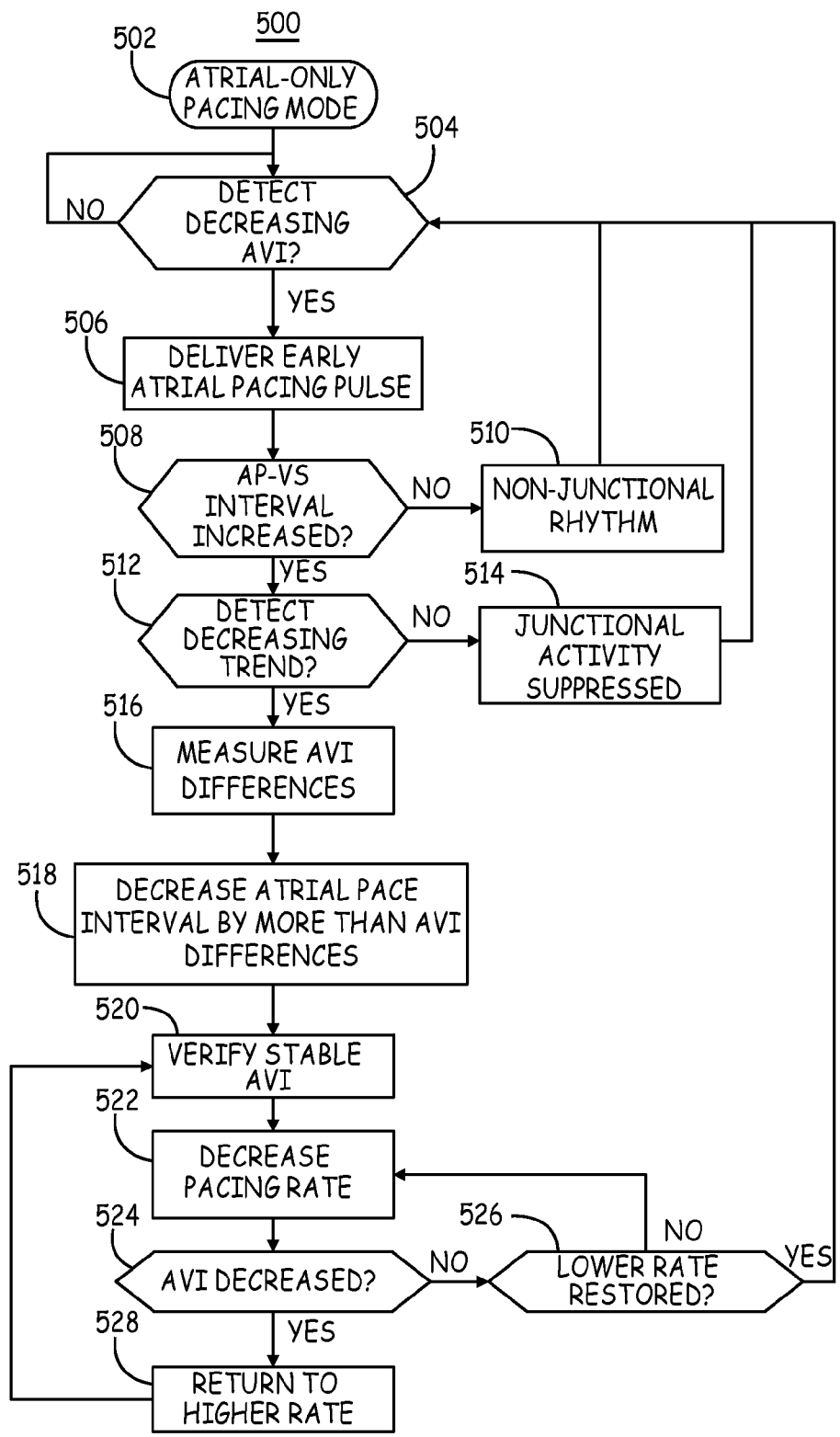
FIG. 6 is a flow chart of an alternative method for controlling atrial pacing including predicting and preventing a junctional rhythm.

FIG. 6 is a flow chart 500 of an alternative method for predicting and preventing a junctional rhythm. During an atrial-only pacing mode (block 502) the AVIs are monitored to detect a decreasing trend. A decreasing trend may be based on a previously defined normal AVI as described above or may be detected through beat-to-beat comparisons of AVI.

If a decreasing trend in AVI is detected, a single atrial pacing pulse is delivered at shortened pacing pulse interval (without adjusting the atrial pacing rate in effect). By delivering a single, early atrial pacing pulse, a pre-junctional rhythm may be interrupted. For example, if the current atrial pacing rate is at approximately 80 beats per minute, i.e. atrial pacing pulses occur at approximately 750 ms intervals, a single atrial pacing pulse may be delivered at an interval 50 to 100 ms earlier, or at an interval of approximately 650 ms to 700 ms from the prior atrial pacing pulse.

The shortened interval at which the single, early atrial pacing pulse is delivered may be a predetermined decrement from an existing atrial pacing interval. Alternatively, the shortened interval may be decreased by an amount that is at least equal to the cumulative amount of time that the AVI has decreased over consecutive cardiac cycles. For example, if the AV intervals measured at block 504 resulting in a detection of a decreasing AVI trend are shortening by approximately 20 ms each cardiac cycle, and five cycles have been measured, the next, single atrial pacing pulse may be delivered at an interval that is at least 100 ms shorter than the current atrial pacing interval. The shortened interval is established based on the cumulative AVI shortening so that the atrial pacing pulse precedes the next expected ventricular sensed event by a time interval sufficient to block the next junctional event. The AVI decrease per beat may be averaged to be less sensitive to beat to beat physiologic variation in the measurement.

After delivering the single early pacing pulse, the subsequent AVI, i.e. the AP-VS interval immediately following the early atrial pacing pulse is measured at block 508. If the AP-VS interval is not increased, the rhythm may not be associated with junctional activity (block 510). The process returns to block 504 and if the AVI continues to decrease, blocks 506 through 508 may be repeated with the early atrial pacing pulse delivered at an even shorter interval.

If the AP-VS interval following the early atrial pacing pulse is increased relative to the AV intervals preceding the early atrial pacing pulse (decision block 508), and is consistent with an expected normal AVI range, the rhythm associated with the decreasing AVI most likely included junctional events. The junctional activity may have been suppressed by the single early atrial pacing pulse. In order to determine if an impending junctional rhythm has been overdriven, the AV intervals are again monitored at block 512. If the decreasing trend in AV intervals is not detected at block 512, the junctional activity has been suppressed (block 514) and the impending junctional rhythm has been averted. The process returns to block 504 to continue to monitor for evidence of a pre-junctional rhythm.

If the decreasing trend in AV intervals is detected again at block 512, subsequent to the early atrial pacing pulse, the junctional activity has not been overdriven or interrupted by the single atrial pacing pulse. The decreasing AV intervals are measured at block 516. The average decrease per cardiac cycle of the AV intervals is determined. The beat-to-beat shortening of the AVI indicates the escape interval of the junctional rhythm. For example if the AVI is shortening by an average of 20 ms per cardiac cycle, the junctional events are occurring at intervals approximately 20 ms shorter than the current atrial pacing rate. The AVI decrease reveals the interval difference of the junctional escape interval and the present pacing interval (or spontaneous atrial beating rate). To overdrive the junctional escape interval, a new atrial pacing interval must be shorter than the difference between the present atrial pacing interval (or intrinsic PP intervals) and the average AVI decrease. Immediate restoration of proper AV synchrony can be achieved by delivering a single early atrial pacing pulse at a shortened interval based on the cumulative shortening of the measured AV intervals as described above. The early atrial pacing pulse is followed by atrial pacing pulses at a new pacing pulse interval set based on the beat-to-beat AVI decrease.

The atrial pacing rate is increased at block 518 based on the measured AV interval differences. For example, the atrial pacing rate is increased by decreasing the atrial pacing pulse interval by a decrement that is greater than the average AVI difference. In this way, an atrial pacing rate is increased to a rate that is likely to be greater than the rate of the junctional activity. As a result, interruption of the junctional activity may occur with greater certainty than when the atrial rate is increased to a randomly selected rate, which may be insufficient, i.e. too slow, to overdrive the junctional activity.

At block 520, the AVI is verified to be stable, i.e. no longer decreasing, and restored to an expected, normal AVI. The atrial pacing rate may then be decreased at block 522, e.g. in a step-wise manner, with each rate decrease followed by a check to verify that the resulting AVI does not decrease again (block 524). If the AVI does not decrease, the atrial pacing rate may continue to be decreased until a lower atrial pacing rate is restored (block 526). The process then returns to block 504 to continue monitoring for a decrease in AVI as evidence of a pre-junctional rhythm.

If the AVI does decrease (block 524), the atrial rate is returned to a higher rate at block 528. The rate may be increased to the lowest atrial pacing rate at which the AVI did not decrease or back to the increased atrial rate applied at block 518. Once the AVI is verified to be stable again (block 520), another attempt may be made to bring the atrial pacing rate back down again. In some embodiments, a minimum period of time of AVI stability may be required before attempting to decrease the atrial pacing rate.

Thus, an implantable device and associated method have been presented in the foregoing description with reference to specific embodiments. It is appreciated that various modifications to the referenced embodiments may be made without departing from the scope of the disclosure as set forth in the following claims.

The invention claimed is:

1. A method for use in an implantable medical device delivering cardiac pacing pulses, the method comprising:
   delivering atrial pacing pulses;
   sensing ventricular events;
   determining a plurality of time intervals between the atrial pacing pulses and subsequently sensed ventricular events;
   detecting a decreasing trend in the plurality of time intervals and detecting a pre-junctional rhythm in response to the decreasing trend; and
   delivering an atrial pacing pulse at a shortened pacing pulse interval in response to detecting the decreasing trend.

2. The method of claim 1 wherein detecting the decreasing trend in the plurality of time intervals comprises:
   setting an expected range for a time interval between an atrial pacing pulse and a subsequently sensed ventricular event;
   detecting a decreasing trend in the plurality of time intervals wherein at least one of the plurality of time intervals is within the expected range.

3. The method of claim 2 wherein setting the expected range comprises:
   detecting an atrial paced rhythm that is sustained for at least a pre-determined period of time; and
   determining an atrial pace-to-ventricular sense time interval range occurring during the sustained atrial paced rhythm.

4. The method of claim 1 further comprising:
   sensing intrinsic atrial events;
   setting a junctional rhythm detection threshold;
   determining a plurality of time intervals between sensed atrial events and sensed ventricular events; and
   detecting a junctional rhythm in response to the plurality of time intervals being less than the junctional rhythm detection threshold.

5. The method of claim 1 further comprising:
   sensing intrinsic atrial events;
   increasing the rate of the atrial pacing pulses in response to the sensing of an atrial event.

6. The method of claim 1 wherein delivering the atrial pacing pulse at a shortened pacing pulse interval comprises increasing a rate of the atrial pacing pulses.

7. The method of claim 6 further comprising:
   sensing a demand signal responsive to a metabolic demand of the patient;
   determining a pacing rate using the demand signal and a rate response control parameter;
   delivering the atrial pacing pulses at the pacing rate;
   wherein increasing the rate of atrial pacing pulses in response to detecting the decreasing trend comprises adjusting the rate response control parameter.

8. The method of claim 6 further comprising:
   storing a frequency of junctional rhythm detections;
   determining if a frequency of the junctional rhythms decreases subsequent to increasing the rate of the atrial pacing pulses.

9. The method of claim 6 further comprising:
   detecting an increasing trend in the plurality of time intervals subsequent to increasing the rate of the atrial pacing pulses; and
   decreasing the rate of the atrial pacing pulses in response to detecting the increasing trend.

10. The method of claim 1 further comprising:
    measuring a time interval between the atrial pacing pulse and a subsequent ventricular sense event;
    detecting a decreasing trend in the plurality of intervals subsequent to the atrial pacing pulse;
    measuring a beat-to-beat difference between the plurality of intervals; and
    increasing the atrial pacing rate in response to detecting the decreasing trend;
    the atrial pacing rate increased by shortening the atrial pacing pulse interval by at least the beat-to-beat difference between the plurality of intervals.

11. The method of claim 1 wherein delivering the atrial pacing pulse comprises shortening a previous atrial pacing pulse interval by at least a cumulative shortening of the plurality of time intervals to establish the shortened pacing pulse interval.

12. An implantable medical device configured to deliver cardiac pacing pulses in a minimum ventricular pacing mode, the device comprising:
an atrial pacing and sensing lead for delivering atrial pacing pulses and sensing atrial signals;
a ventricular pacing and sensing lead for delivering ventricular pacing pulses and sensing ventricular signals;
a sensing module coupled to the atrial and ventricular pacing and sensing leads, the sensing module responsive to depolarizations of a heart;
a pulse generator producing cardiac stimulation pulses delivered via the atrial and ventricular pacing and sensing leads; and
a control module coupled to the sensing module and the therapy delivery module, the control module configured to:
determine a plurality of time intervals between atrial pacing pulses and subsequently sensed ventricular events;
detect a decreasing trend in the plurality of time intervals and detect a pre-junctional rhythm in response to the decreasing trend; and
deliver an atrial pacing pulse at a shortened pacing pulse interval in response to detecting the decreasing trend.

13. The device of claim 12 further comprising a memory storing an expected range for an interval between an atrial pacing pulse and a subsequently sensed ventricular event;
wherein detecting the decreasing trend includes detecting a decreasing trend when at least one of the plurality of time intervals is within the expected range.

14. The device of claim 13 wherein the control module is further configured to:
detect an atrial paced rhythm that is sustained for at least a pre-determined period of time;
determine an atrial pace-to-ventricular sense time interval range occurring during the sustained atrial paced rhythm; and
store the atrial pace-to-ventricular sense time interval range as the expected range.

15. The device of claim 12 further comprising:
a memory storing a junctional rhythm detection threshold;
wherein the control module is further configured to determine a plurality of time intervals between sensed atrial events and sensed ventricular events and detect a junctional rhythm in response to the plurality of time intervals being less than the junctional rhythm detection threshold.

16. The device of claim 12 wherein the control module is further configured to increase a rate of the atrial pacing pulses in response to sensing an atrial event.

17. The device of claim 12 wherein delivering the atrial pacing pulse at a shortened pacing pulse interval comprises increasing a rate of the atrial pacing pulses delivered by the pulse generator.

18. The device of claim 17 further comprising:
a demand sensor coupled to the control module and providing a demand signal responsive to a metabolic demand of the patient;
wherein the control module is further configured to:
determine a pacing rate using the demand signal and a rate response control parameter;
control the pulse generator to deliver the atrial pacing pulses at the pacing rate;
wherein increasing the rate of the atrial pacing pulses in response to detecting the decreasing trend comprises adjusting the rate response control parameter.

19. The device of claim 17 wherein the control module is further configured to determine a frequency of junctional rhythm detections and to determine if the frequency of the junctional rhythm detections decreases subsequent to increasing the rate of the atrial pacing pulses.

20. The device of claim 16 wherein the control module is further configured to:
detect an increasing trend in the plurality of time intervals subsequent to increasing the rate of the atrial pacing pulses; and
decrease the rate of the atrial pacing pulses in response to detecting the increasing trend.

21. The device of claim 12 wherein the control module is further configured to:
measure a time interval between the atrial pacing pulse and a subsequent ventricular sense event;
detect a decreasing trend in the plurality of intervals subsequent to the atrial pacing pulse;
measure a beat-to-beat difference between the plurality of intervals; and
increase the atrial pacing rate in response to detecting the decreasing trend;
the atrial pacing rate being increased by shortening the atrial pacing pulse interval by at least the beat-to-beat difference between the plurality of intervals.

22. The device of claim 12 wherein the control module is further configured to establish the shortened pacing pulse interval by decreasing a previous atrial pacing pulse interval by at least a cumulative shortening of the plurality of time intervals.

23. A non-transitory computer readable medium storing a set of instructions which when implemented in an implantable medical device processor cause the device to:
deliver atrial pacing pulses;
sense ventricular events;
determine a plurality of intervals between an atrial pacing pulse and a subsequently sensed ventricular event;
detect a decreasing trend in the plurality of time intervals and detect a pre-junctional rhythm in response to detecting the decreasing trend; and
deliver an atrial pacing pulse at a shortened pacing pulse interval in response to detecting the decreasing trend.

* * * * *